United States Patent [19]

Ohbayashi et al.

[11] Patent Number: 4,529,690
[45] Date of Patent: Jul. 16, 1985

[54] SILVER HALIDE COLOR PHOTOGRAPHIC LIGHT-SENSITIVE MATERIAL

[75] Inventors: Keiji Ohbayashi; Shinichi Nakamura, both of Hino, Japan

[73] Assignee: Konishiroku Photo Industry Co., Ltd., Tokyo, Japan

[21] Appl. No.: 643,822

[22] Filed: Aug. 23, 1984

[30] Foreign Application Priority Data

Aug. 30, 1983 [JP] Japan ................................ 58-158315

[51] Int. Cl.³ .......................... G03C 7/26; G03C 1/02
[52] U.S. Cl. .................................... 430/543; 430/550; 430/551; 430/564; 430/599
[58] Field of Search ............... 430/543, 550, 546, 551, 430/564, 599, 606, 607, 621, 631, 638

[56] References Cited

U.S. PATENT DOCUMENTS 3,043,697  7/1962  Forsgard ............................ 430/607
4,004,928  1/1977  Miyazawa et al. .................. 430/512

Primary Examiner—Mary F. Downey
Attorney, Agent, or Firm—Jordan B. Bierman

[57] ABSTRACT

A color photographic element contains a compound of the following formula:

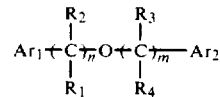

wherein $R_1$, $R_2$, $R_3$ and $R_4$ each represent hydrogen atom, or an alkyl or aryl group; $Ar_1$ and $Ar_2$ each represent an aryl group; and n and m each represent 1 or 2. The color element containing the above compound displays excellent sensitivity, gradation, and color-developability even when developing it with a color developer not substantially containing any benzyl alcohol.

9 Claims, No Drawings

SILVER HALIDE COLOR PHOTOGRAPHIC LIGHT-SENSITIVE MATERIAL

BACKGROUND OF THE INVENTION

1. Field of the Invention

The invention relates to silver halide color photographic light-sensitive materials and more particularly to a silver halide color photographic light-sensitive material capable of displaying such an excellent photographic characteristics as sensitivity, gradation, color-developability and the like even when developing it with a color-developer not substantially containing any benzyl alcohol.

2. Description of the Prior Art

Conventionally, a silver halide color photographic light-sensitive material is color-developed, after exposed imagewise, with an aromatic primary amine color developing agent in the presence of cyan, magenta and yellow couplers. In this process, the silver halide microcrystals of the exposed silver halide color photographic light-sensitive material are reduced by the color developing agent and the oxidants simultaneously produced of the color developing agent take part in a coupling reaction with the couplers, so that a color photographic image comprising cyan, magenta and yellow dyes may be formed.

In this type of processes, a silver halide emulsion layer contains couplers in advance, that is, the so-called coupler-in-emulsion type color developing process is popularly used.

Cyan, magenta and yellow couplers each to be used in this coupler-in-emulsion type color developing process should be fixed into the respective silver halide emulsion layers which are selectively blue, green and red sensitive, so as to avoid the mixing of color. For these couplers, those couplers having, in their molecules, a long-chain aliphatic group serving as a ballast group are used. Because these couplers each have a hydrophobic ballast group, the couplers are usually dissolved in a high boiling organic solvent and are then dispersed, in the form of oil-droplet like colloidal particles, into an aqueous gelatin solution.

A silver halide color photographic material containing such couplers having the hydrophobic group is relatively slow in the permeability of a color developing agent into the couplers and is accordingly slow in the color developing speed. Therefore, in order to accelerate the speed, a variety of permeating agents are studied and used. Among them, benzyl alcohol is popularly used as this kind of permeating agent. When processing with a color developer containing it, an excellent color developability of couplers may be enjoyed and it is also possible to obtain a color photographic image capable of displaying the photographic characteristics excellent in sensitivity, gradation, a maximum density and the like.

Now, in order to obtain an excellent color developability in the process of color developing a color photographic light-sensitive material with a color developer containing benzyl alcohol, the contents of benzyl alcohol is normally 10 to 15 m or more per liter of color developer. Benzyl alcohol is low in solubility to water, and it has, therefore, been necessary in an ordinary case to make benzyl alcohol soluble by adding a reasonable amount of such a polyhydric alcohol as ethylene glycol, diethylene glycol, triethylene glycol, glycerol or the like to serve as an auxiliary solvent.

On the other hand, benzyl alcohol is one of the substances useful for a color developing process, however, this substance and polyhydric alcohols are at a high level of such an environmental pollution as a biochemical oxygen demand (BOD), a chemical oxygen demand (COD) and the like. It is, therefore, desired that they are to be used as little as possible or not to be used at all, if possible. In particular, if benzyl alcohol can be limited to use in the amount of not more than 8 m per liter of a color developer, a polyhydric alcohol can also be avoided to use as the auxiliary solvent of benzyl alcohol. In addition to the above, there is a secondary advantage that the environmental pollution level may be lowered.

Accordingly, there have been the demands for and studies on the developments of photographic processes in which a silver halide color photographic light-sensitive material may be color-developed with a color developer containing benzyl alcohol as little as possible or not containing it at all and the color developability of couplers is not degraded, and the developments of the abovementioned silver halide color photographic light-sensitive materials. For example, Japanese Patent Publication Open to Public Inspection (hereinafter called Japanese Patent O.P.I. Publication) No. 50536/1983 has proposed that a light-sensitive material containing 1-aryl-3-pyrazolidone is processed with a color developer to which benzyl alcohol is added in the amount of 2 to 8 ml per liter of the color developer. According to the technique described in this patent publication, any color developability and the density of dyes to a given amount of silver developed cannot be improved and the characteristic curve shows such an disadvantage particularly in the region of a medium density, though a color developing agent may be accelerated to diffuse from the color developer into the emulsion layers of the light-sensitive material.

OBJECT AND SUMMARY OF THE INVENTION

This invention was made in consideration of the abovementioned situations of the prior art. It is, accordingly, an object of the invention to provide a silver halide color photographic light-sensitive material capable of displaying the excellent photographic characteristics in color density, sensitivity, gradation and the like, with very little dependence on the kinds of couplers and high boiling organic solvents used therein, even when color-developing with a color developer not substantially containing benzyl alcohol.

The abovementioned object of the invention can be achieved in a silver halide color photographic light-sensitive material comprising a support bearing thereon photographic component layers including at least one silver halide emulsion layer, wherein at least one of the photographic component layers contains at least one kind of the compounds having the following Formula [I]:

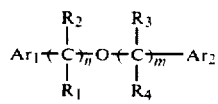

Formula [I]

wherein, $R_1$, $R_2$, $R_3$ and $R_4$ each represent hydrogen, or an alkyl or aryl group $Ar_1$ and $Ar_2$ each represent an aryl group; and, n and m each have an integer of 1 or 2.

DETAILED DESCRIPTION OF THE INVENTION

Alkyl groups represented by $R_1$, $R_2$, $R_3$ and $R_4$ in Formula [I] are those preferably having 1 to 6 carbon atoms, including, for example, methyl, ethyl, propyl or butyl group and the like. These alkyl groups may respectively be the same with or the different from each other.

Aryl groups represented by $Ar_1$ and $Ar_2$ in Formula [I] include, for example, phenyl or naphthyl group and the like, and phenyl group is particularly preferred. The aryl group may be allowed to have a substituent. The substituents include, for example, an alkyl group such as methyl, ethyl, isopropyl, t-butyl, t-amyl, dodecyl, or octyl group and the like; phenyl group; a halogen atom such as chlorine or bromine atom and the like; a alkoxy group such as methoxy or ethoxy group and the like; nitro group; amino group; cyano group; hydroxyl group; carbamoyl group; sulfonamide group; alkyl carbonyl oxy group; aryl carbonyl oxy group; a cyclo alkyl group such as 5 to 7-membered cyclo alkyl such as cyclo hexyl group; and amido group such as dodecylcarbonyl amino group.

Among those represented by $R_1$, $R_2$, $R_3$ and $R_4$ in Formula [I], the preferred ones include hydrogen, methyl group and butyl group, and the more preferred one is hydrogen.

Among those represented by $Ar_1$ and $Ar_2$ in Formula [I], the particularly preferred one is phenyl group.

The following are the exemplified compounds having Formula [I] which are to be used in the invention, and it is, however, to be understood that the invention shall not be limited thereto.

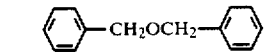  A-1

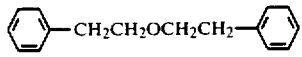  A-2

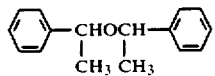  A-3

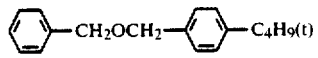  A-4

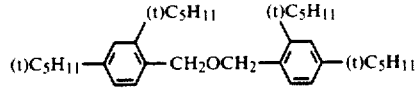  A-5

  A-6

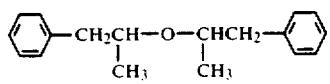  A-7

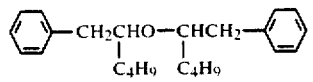  A-8

-continued

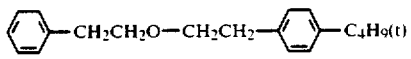  A-9

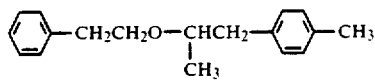  A-10

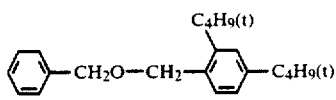  A-11

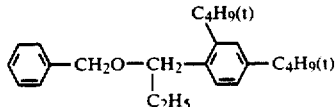  A-12

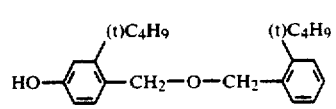  A-13

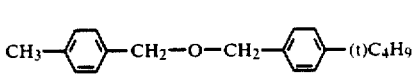  A-14

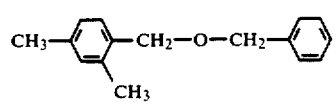  A-15

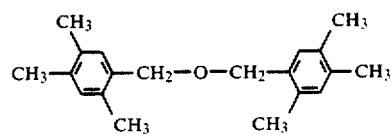  A-16

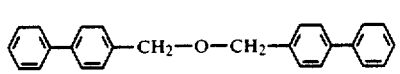  A-17

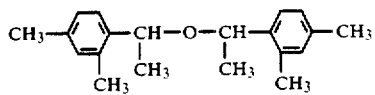  A-18

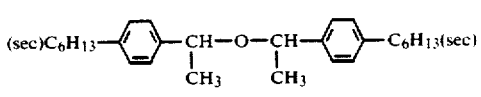  A-19

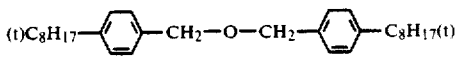  A-20

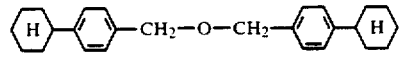  A-21

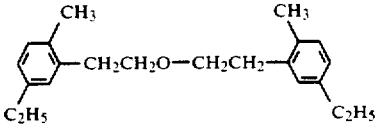  A-22

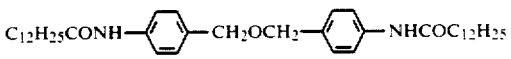  A-23

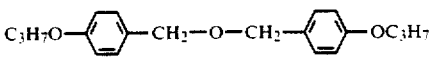  A-24

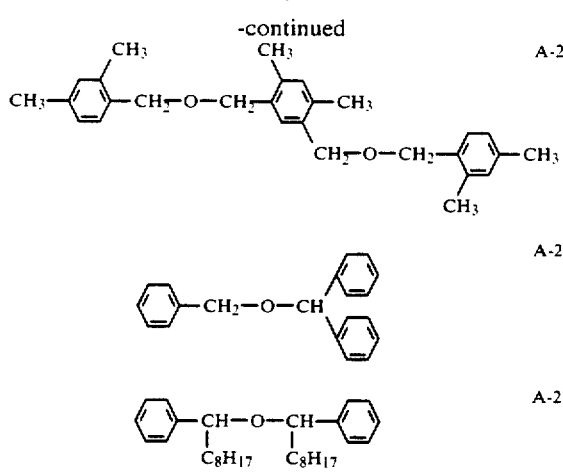

The compounds of the invention may be synthesized according to the well-known processes, though they are available on the market. For example, they may be obtained through a dehydration reaction of corresponding benzyl alcohol, through a reaction of benzyl alcohol with a benzyl halide in the presence of alkalies, or through a substitutive reaction to benzyl ether.

The following examples are exemplary of synthesized compounds of the invention.

Synthetic Example 1 (Synthesis of Compound A-6)

In an egg-plant type flask having the capacity of 100 ml, 8.2 g of p-t-butyl benzyl alcohol and 0.1 g of sulfamic acid were added to put in an oil bath, and were then agitated with heating at 150° C. and at reduced pressure. After heating for about one hour, the drops of sulfamic acid-water liquid were left in the bottom of the flask, and the supernatant liquid was taken out. The remaining liquid was washed out with ethyl acetate and was then added to the supernatant liquid. The liquid obtained was concentrated at reduced pressure and was then distilled at reduced pressure of 0.07 mmHg at 160° to 175° C., and thus, 6.2 g of a colorless liquid substance was obtained as an object.

The results of the elementary analyses, the NMR and IR measurements thereof proved that the compound supports the structure of the object.

Synthetic Example 2 (Synthesis of Compound 16)

A mixture of 240 g of 1,2,4-trimethyl benzene, 178 g of formalin and 1,250 ml of concentrated hydrochloric acid was heated at 60 to 65° for six hours. After cooling, the product was extracted with petroleum ether and was then distilled with heating at the temparature from 40° C. to 105° C. The distillates were collected.

(Yield=246 g; 2,4,5-trimethyl benzyl chloride)

Next, a mixture of 16.9 g of 2,4,5-trimethyl benzyl chloride, 11g of anhydrous sodium carbonate and 100 ml of pure water was refluxed with heating for about 12 hours. After cooling, the solid products were filtrated and the mother liquor was concentrated with heating and was further recrystallized with chloroform. Yeild was 4.8 g. The results of the NMR and IR measurements and the elementary analyses thereof proved that the compound supports the structure of the object.

The compounds having Formula [I] (hereinafter called the compounds of the invention) can be added to any one of the photographic component layers constituting a silver halide color photographic light-sensitive material. Such photographic component layers include, for example, a blue-sensitive, green-sensitive or red-sensitive emulsion layer, a layer adjacent to an emulsion layer such as an interlayer, a filter layer and a subbing layer, the bottom layer adjoining the subbing layer, a protective layer, and the like.

The compounds of the invention may be added to any one of the abovementioned layers or more than two layers thereof. It is preferred when the compounds of the invention are added to the silver halide emulsion layers.

Commonly, the compounds of the invention are oil-soluble, and it is generally preferable that they are dissolved in a high boiling solvent, and if required a low boiling solvent in combination, and are then dispersed to add into such a hydrophilic colloidal solution as a gelatin solution, in one of the processes described in U.S. Pat. Nos. 2,322,027, 2,801,170, 2,801,171, 2,272,191, and 2,304,940. In this instance, it is also warrantable at all to use couplers, hydroquinone derivatives, ultra-violet absorbents or the like in combination. It is further justifiable to use, in combination, two or more kinds of the compounds of the invention.

How to add the compounds of the invention will be described in more detail.

One or more kinds of the compounds of the invention with, if required, couplers, hydroquinone deriatives, ultra-violet absorbents, or the like, are dissolved in a high boiling organic solvent such as an organic acid amide, a carbamate, an ester, a ketone, a hydrocarbon, a urea derivative and the like and particularly, di-n-butyl phthalate, di-octyl phthalate di-lauryl phthalate, tricresyl phosphate, trioctyl phosphate, di-isooctyl azelate, di-n-butyl sebacate, dekalin, N,N-diethyl laurylamide, n-pentadecylphenyl ether, fluoroparaffin or the like; and, if required, in a low boiling organic solvent such as ethyl acetate, butyl acetate, cyclohexanol, cyclohexane, tetrahydrofran or the like, (These high boiling organic solvents and low boiling organic solvents may be used either independently or in combination.); the obtained solution is mixed with an aqueous solution containing an anionic surfactant such as alkylbenzene sulfonic acid, alkylnaphthalene sulfonic acid and sulfoalkyl succinate, and/or a nonionic surfactant such as sorbitan sesquioleic acid ester and sorbitan monolauric acid ester; the mixture is dispersed upon emulsifying by a high-speed rotary mixer, colloid mill, super-sonic dispersing means or the like; and the dispersion solution is then added to a hydrophilic colloidal solution, so as to be used.

In the case that the hydrophilic colloidal solution is a silver halide emulsion, a silver halide to be described later is contained therein. Thus obtained hydrophilic colloidal solution is to be coated in a variety of the well-known methods so that a silver halide color photographic light-sensitive material may be obtained.

The amount of the compounds of the invention to be added is preferably 5 to 500 wt % to an amount of couplers and more preferably 10 to 150 wt % thereto when adding them to a silver halide emulsion layer containing couplers, and is preferably within the range of about 0.01 to 2 g and more preferably within the range of 0.05 to 0.5 g per sq. meter of an interlayer or the like not containing any coupler when adding them to such a layer.

The photographic emulsion layers of a silver halide color photographic light-sensitive material of the invention contain the dye-forming couplers capable of forming cyan, magenta and yellow dyes each through a coupling reaction with the oxidants of aromatic primary amine color developing agent in a color developing process.

Among these dye-forming couplers, the yellow dye-forming couplers include those of a benzoyl acetanilide type pivaloyl acetanilide type, which can be a 2-equivalent type in which carbon atom in a coupling position is substituted by a substituent capable of splitting off at the time of the coupling reaction, that is the so-called split-off radical); the magenta dye-forming couplers include those of a 5-pyrazolone type, a pyrazolotriazole type, a pyrazolinobenzimidazole type, an indazolone type, which can be a 2-equivalent type having a split-off radical; and the cyan dye-forming couplers include those of a phenol type, naphthol type, a pyrazoloquinazolone type, which can be a 2-equivalent type having a split-off radical.

Among these dye-forming couplers, yellow dye-forming couplers are described, for example, in U.S. Pat. Nos. 2,778,658, 2,875,057, 2,908,573, 2,908,513, 3,227,155, 3,227,550, 3,253,924, 3,265,506, 3,277,155, 3,341,331, 3,369,895, 3,384,657, 3,408,194, 3,415,652, 3,447,928, 3,551,155, 3,582,322 and 3,725,072; West German Pat. Nos. 1,547,868, 2,057,941, 2,162,899, 2,163,812, 2,213,461, 2,219,917, 2,261,361 and 2,263,875; Japanese Patent Examined Publication No. 13576/1974, Japanese Patent Publication Open to Public Inspection (hereinafter referred to as Japanese Patent O.P.I. Publication) Nos. 29432/1973, 66834/1973, 10736/1974, 122335/1974, 28834/1975, 132926/1975, 144240/1980 and 87041/1981.

And, magenta dye-forming couplers are described, for example, in U.S. Pat. Nos. 2,600,788, 3,061,432, 3,062,653, 3,127,269, 3,311,476, 3,152,896, 3,419,391, 3,519,429, 3,558,318, 3,684,514, 3,705,896, 3,888,680, 3,907,571, 3,928,044, 3,930,861, 3,930,816 and 3,933,500; Japanese Patent O.P.I. Publication Nos. 29639/1974, 111631/1974, 129538/1974, 11234/1976, 58922/1977, 624541/1980, 118034/1980, 38643/1981 and 135841/1981; Japanese Patent Examined Publication Nos. 60479/1971, 34937/1977, 29421/1980 and 35696/1980; British Pat. No. 1,247,493; Belgian Pat. No. 792,525; and West German Pat. No. 2,156,111.

Further, cyan dye-forming couplers are described, for example, in U.S. Pat. Nos. 2,369,929, 2,423,730, 2,434,272, 2,474,293, 2,698,794, 2,706,684, 2,772,162, 2,801,171, 2,895,826, 2,908,573, 3,034,892, 3,046,129, 3,227,550, 3,253,294, 3,311,476, 3,386,301, 3,419,390, 3,458,315, 3,46,563, 3,516,831, 3,560,212, 3,582,322, 3,583,971, 3,591,383, 3,619,196, 3,632,347, 3,652,286, 3,737,326, 3,758,308, 3,779,768 and 3,839,044; West German Pat. Nos. 2,163,811 and 2,207,468; Japanese Patent Examined Publication Nos. 27563/1964 and 28836/1970; Japanese Patent O.P.I. Publication Nos. 37425/1972, 10135/1975, 25228/1975, 112038/1975, 117422/1975, 130441/1975, 109630/1978, 32071/1980, 163537/1980, 1938/1981, 13643/1981, 29235/1981, 65134/1981 and 104333/1981; and Research Disclosure No. 14853/1976; or the like.

Concrete examples of the dye-forming couplers used for the invention are shown below, but the invention is not limited thereto.

(Y-1)
α-(4-carboxyphenoxy)-α-pivalyl-2-chloro-5-[γ-(2,4-di-t-amylphenoxy)butylamide] acetanilide (Y-2)
α-benzoyl-2-chloro-5-[α-(2,4-di-t-amylphenoxy)butylamide] acetanilide (Y-3)
α-benzoyl-2-chloro-5-[α-(dodecyloxycarbonyl)ethoxycarbonyl] acetanilide (Y-4)
α-(4-carboxyphenoxy)α-pivalyl-2-chloro-5-[α-(3-pentadecylphenoxy)butylamide] acetanilide.

(Y-5)
α-(1-benzyl-2,4-dioxo-3-imidazolidinyl)-α-pivalyl-2-chloro-5-[γ-2,4-di-t-amylphenoxy)butylamide] acetanilide (Y-6)
α-[4-(1-benzyl-2-phenyl-3,5-dioxo-1,2,4-triazolidinyl)]-α-pyvalyl-2-chloro-5-[γ-2,4-di-t-amylphenoxy)-butylamide] acetanilide (Y-7)
α-acetoxy-α-{3-[α-(2,4-di-t-amylphenoxy)butylamide]-benzoyl}-2-methoxyacetanilide (Y-8)
α-{3-[α-(2,4-di-t-amylphenoxy)butylamide]benzoyl}-2-methoxyacetanilide (Y-9)
α-[4-(4-benzyloxyphenylsulfonyl)phenoxy]α-pivalyl-2-chloro-5-[γ-(2,4-di-t-amylphenoxy)butylamide] acetanilide (Y-10)
α-pivalyl-α-(4,5-dichloro-3-(2H)-pyridazo-2-yl)-2-chloro-5-[(hexadecyloxycarbonyl)methoxycarbonyl] acetanilide (Y-11)
α-pivalyl-α-[4-(p-chlorophenyl)-5-oxo-$\Delta^2$-tetrazoline-1-yl]-2-chloro-5-[α-(dodecyloxycarbonyl)ethoxycarbonyl] acetanilide (Y-12)
α-(2,4-dioxo-5,5-dimethyloxazolidine-3-yl)-α-pivalyl-2-chloro-5-[α-(2,4-di-t-amylphenoxy)butylamide] acetanilide (Y-13)
α-pivalyl-α-[4-(1-methyl-2-phenyl-3,5-dioxo-1,2,4-triazolidinyl)]-2-chloro-5-[γ-(2,4-di-t-amylphenoxy)-butylamide] acetanilide (Y-14)
α-pivalyl-α-[4-p-ethylphenyl)-5-oxo-$\Delta^2$-tetrazolyl-1-yl]-2-chloro-5-[γ-(2,4-di-t-amylphenoxy)butylamide] acetanilide (Y-15)
α-(1-benzyl-2-phenyl-3,5-dioxo-1,2,4-triazolidinyl)-α-pivalyl-2-chloro-5-[α-(dodecyloxycarbonyl)ethoxycarbonyl] acetanilide (M-1)
1-(2,4,6-trichlorophenyl)-3-[3-(2,4-di-t-amylphenoxyacetamide)benzamide]-5-pyrazolone (M-2)
1-(2,4,6-trichlorophenyl)-3-(3-dodecylsuccinimidebenzamide)-5-pyrazolone (M-3)
4,4'-methylenebis{1-2,4,6-trichlorophenyl)-3-[3-(2,4-di-t-amylphenoxyacetamide)benzamide]-5-pyrazolone (M-4)
1-(2,4,6-trichlorophenyl)-3-(2-chloro-5-octadecylsuccinimideanilino)-5-pyrazolone (M-5)
1-(2-chloro-4,6-dimethylphenyl)-3-{3-[α-(3-pentadecylphenoxy)butylamide]benzamide}-5-pyrazolone (M-6)
1-(2,4,6-trichlorophenyl)-3-(2-chloro-5-octadecylcarbamoylanilino)-5-pyrazolone (M-7)
3-ethoxy-1-{4-[α-(3-pentadecylphenoxy)butylamide]-phenyl}-5-pyrazolone
(M-8)
1-(2,4,6-trichlorophenyl)-3-(2-chloro-5-tetradecaneamideanilino)-5-pyrazolone
(M-9)
1-(2,4,6-trichlorophenyl)-3-{2-chloro-5-[α-(3-t-butyl-4-hydroxyphenoxy)tetradecaneamide]anilino}-5-pyrazolone
(M-10)
1-(2,4,6-trichlorophenyl)-3-[3-(2,4-di-t-amylphenoxyacetamide)benzamide]-4-acetoxy-5-pyrazolone
(M-11)
1-(2,4,6-trichlorophenyl)-3-[3-(2,4-di-t-amylphenoxyacetamide)benzamide]-4-ethoxycarbonyloxy-5-pyrazolone
(M-12)
1-(2,4,6-trichlorophenyl)-3-[3-(2,4-di-t-amylphenoxyacetamide)benzamide]-4-(4-chlorocinnamoyloxy)-5-pyrazolone
(M-13)
4,4'-benzylidenebis[1-(2,4,6-trichlorophenyl)-3-{2-chloro-5-[γ-(2,4-di-t-amylphenoxy)-butylamide]anilino)}-5-pyrazolone]
(M-14)
4,4'-benzylidenebis[1-(2,3,4,5,6-pentachlorophenyl)-3-{2-chloro-5-[γ-(2,4-di-t-amylphenoxy)-butylamide]anilino}-5-pyrazolone]
(M-15)
4,4'-(2-chloro)benzylidenebis[1-(2,4,6-trichlorophenyl)-3-(2-chloro-5-dodecylsuccinimideanilino-5-pyrazolone]
(M-16)
4,4'-methylenebis[1-(2,4,6-trichlorophenyl)-3-{3-[α-(2,4-di-t-amylphenoxy)butylamide]benzamide}-5-pyrazolone]
(M-17)
1-(2,6-dichloro-4-methoxyphenyl)-3-(2-methyl-5-acetamideanilino)-5-pyrazolone
(M-18)
1-(2-chloro-4,6-dimethylphenyl)-3-(2-methyl-5-chloroanilino)-5-pyrazolone
(M-19)
1-(2,4,6-trichlorophenyl)-3-(4-nitroanilino)-5-pyrazolone
(M-20)
1-(2,4,6-trichlorophenyl)-3-(2-chloro-5-octadecenylsuccinimideanilino)-5-pyrazolone
(M-21)
1-(2,4,6-trichlorophenyl)-3-(2-chlorotridecaneamideanilino)-5-pyrazolone
(M-22)
1-(2,4,6-trichlorophenyl)-3-(2-chloro-5-tetradecaneamide)anilino-4-(2-dodecylamide)phenylthio-5-pyrazolone
(M-23)
1-(2,4,6-trichlorophenyl)-3-[2-chloro-5-(2,4-di-t-amylphenoxy)acetamide]anilino-4-phenylthio-5-pyrazolone
(M-24)
1-(2,4,6-trichlorophenyl)-3-(2-chloro-5-tetradecaneamide)anilino-4-(2-methoxy)phenylthio-5-pyrazolone
(M-25)
1-(2,4,6-trichlorophenyl)-3-(2-chloro-5-tetradecaneamide)anilino-4-benzylthio-5-pyrazolone
(C-1)
1-hydroxy-N-[δ-2,4,-di-t-amylphenoxy)butyl]-2-naphthamide
(C-2)
2,4-dichloro-3-methyl-6-(2,4-di-t-amylphenoxyacetamide)phenol
(C-3)
2,4-dichloro-3-methyl-6-[α-(2,4-di-t-amylphenoxy)-butylamide]phenol
(C-4)
1-hydroxy-4-(3-nitrophenylsulfonamide)-N-[δ-(2,4-di-t-amylphenoxy)butyl]-2-naphthamide
(C-5)
1-hydroxy-4-[(δ-methoxyethyl)carbamoyl]methoxy-N-[δ-(2,4-di-t-amylphenoxy)butyl]-2-naphthamide
(C-6)
1-hydroxy-4-(isopropylcarbamoyl)methoxy-N-dodecyl-2-naphthamide
(C-7)
2-pa-fluorobutylamide-5-[α-(2,4-di-t-amylphenoxy)hexaneamide]phenol
(C-8)
1-hydroxy-4-(4-nitrophenylcarbamoyl)oxy-N-[δ-(2,4-di-t-amylphenoxy)butyl]-2-naphthamide
(C-9)
2-(α,α,β,β-tetrafluoropropionamide-5-[α-(2,4-di-t-amylphenoxy)butlamide]phenol
(C-10)
1-hydroxy-N-dodecyl-2-naphthamide
(C-11)
1-hydroxy-(4-nitro)phenoxy-N-[δ-(2,4-di-t-amylphenoxy)butyl]-2-naphthamide
(C-12)
1-hydroxy-4-(1-phenyl-5-tetrazolyloxy)-N-[δ-(2,4-di-t-amylphenoxy)butyl]-2-naphthamide
(C-13)
2-(α,α,β,β-tetrafluoropropionamide)-4-β-chloroethoxy-5-[α-(2,4-di-t-amylphenoxy)butylamide]phenol
(C-14)
2-chloro-3-methyl-4-ethylcarbamoylmethoxy-6-[α-(2,4-di-t-amylphenoxy)butylamide]phenol
(C-15)
2-benzoylamino-4-chloro-5-[α-(4-butanesulfonaminophenoxy)-α-dodecyl-acetylamino]phenol
(C-16)
2-(4-cyanobenzoyl)amino-4-chloro-5-[α-2-dodecylsulfonamino)-α-dimethyl-acetylamino]phenol
(C-17)
2-(pa-fluorobenzoyl)amino-4-chloro-5-[α-(3-dodecylsulfonamino)-α-butyl-acetylamino]phenol
(C-18)
2-(pa-fluorobenzoyl)amino-4-chloro-5-[(2,4-di-t-butylphenoxy)acetylamino]phenol
(C-19)
2-benzoylanilino-4-chloro-5-[(4-dodecyloxy)phenoxybutaneamide]phenol When adding the compounds of the invention into silver halide color photographic light-sensitive materials with high boiling point organic solvents, it is preferable to use such a high boiling point organic solvent whose boiling point is over 170° C. as is incapable of mixing with water. Examples of the above organic solvents are phthalic acid esters such as dimethyl phthalate, dibutyl phthalate, dioctyl phthalate, diallyl phthalate, dinonyl phthalate, dilauryl phthalate, dibenzyl phthalate, diphenyl phthalate or the like; phosphoric acid esters such as diphenyl phosphate, tricresyl phosphate, triphenyl phosphate, dioctyl butyl phosphate, trihexyl phosphate, trioctyl phosphate or the like; citric acid esters such as acetyl tributyl citrate, tributyl citrate or the like; benzoic esters such as butyl benzoate, octyl benzoate or the like; alkyl amides such as diethyllauryl amide or the like; sebacic acid esters such as diethylhexyl sebacate or the like; stearic acid esters such as butyl stearate or the like; maleic acid esters such as dinonyl maleate or the like; succinic acid esters such as diethyl succenate or the like; adipic acid esters such as dioctyl adipate or the like; pyrrolidones such as N-dodecyl pyrrolidone or the like.

Examples of low boiling point (about 30°–150° C.) organic solvents used with above described high boiling solvent, as auxiliary solvents, are a lower acetyl acetate such as ethyl acetate, butyl acetate, β-ethoxyethyl acetate or the like, butyl alcohol, methyl isobutylketone, chloroform, hexane, cyclohexane, ethylene glycol, acetone, ethanol, dioxane, dimethylformamide and the like.

Silver halides contained in the silver halide emulsion layers of the invention may be any one of such silver halides as silver iodobromide, silver chlorobromide, silver bromide, silver chloroiodobromide, silver chloride, silver chloroiodide.

These silver halides may be prepared by an ammonia method, a neutral method or an acid method or may be produced by double-jet precipitation, normal precipitation, reverse precipitation or conversion precipitation. It may be effectively used for the invention when silver halide particles have inside thereof different halogen compositions with or without a boundary between them.

As for binders to be used for the constituent layer of the silver halide color photographic light-sensitive material of the invention, alkali processed gelatin or acid processed gelatin and the like are most commonly used. And, the gelatins are used also in combination with gelatin derivatives such as phthalic gelatin, phenylcarbamoyl gelatin, albumin, agar, gum arabic, alginic acid, a partially hydrolyzed cellulose derivative, partially hydrolyzed polyvinyl acetate, polyacrylamide, polyvinyl alcohol, polyvinyl pyrrolidone, and the copolymers of these vinyl compounds.

Silver halide emulsion of the invention may be chemically sensitized by noble metal sensitizing, sulphur sensitizing, selenium sensitizing, reduction sensitizing and the like. Noble metal sensitizers include salts of noble metals such as ruthenium, rhodium, palladium, iridium, platinum, gold and the like, which are, for example, ammonium chloropalladate, potassium chloroplatinate, potassium chloropalladite, and potassium chloroaurate or the like. Sulphur sensitizers include activated gelatin and labile sulphur compounds such as sodium thiosulphate and the like. Selenium sensitizing is done by selenium compounds. Reduction sensitizing is made under a low pAg with a stannous salt, polyamine and the like.

Further, these silver halide emulsions may be spectrally sensitized by various sensitizers so as to be light-sensitive to a desired spectral region. As for preferable sensitizers, cyanine dyes, merocyanine dyes and compound cyanine dyes may be used singly or in combination. These dyes are described, for example, in U.S. Pat. Nos. 1,939,201, 2,072,908, 2,739,149, 2,213,995, 2,493,748, 2,519,001, West German Pat. No. 929,080 and British Pat. No. 505,979. Above described various spectral sensitizers are used also for other purposes, for example, to prevent fog and deterioration of photographic performance caused by the storage of silver halide color photographic light-sensitive materials and to control development such as gradation control and the like.

To the constituent layers of the silver halide color photographic light-sensitive material of the invention are added, if necessary, chemical sensitizers such as a thioether compound, quaternary ammonium salt compound, polyalkylene oxide compound or the like, and stabilizers such as triazoles, imidazoles, azaindenes, benzothiazolium compounds, zinc compounds, cadmium compounds, mercaptans to the degree so as not to deteriorate the effect of the invention.

Further added to the constituent layer of the silver halide color photographic light-sensitive material of the invention are various photographic additives. They are ultraviolet absorbents such as benzophenone compounds and benzotriazole compounds, development accelerators such as 1-aryl-3-pyrazolidone compounds, surfactants such as sodium alkylnaphthalene sulfonate, sodium alkylbenzene sulfonate, sodium salt of sulfoalkylsuccinate, polyalkylene compounds or the like, water soluble antiirradiation dyes such as azo compounds, styryl compounds, oxonol compounds, triphenylmethane compounds or the like, hardners such as s-triazine compounds substituted by a halogen, active vinyl compounds, ethyleneimino compounds, epoxy compounds, water soluble alminium salts or the like, physical property improving agent for coating layers such as glycerol, polyalkylene glycol, aqueous polymer dispersion (latex), solid or liquid paraffin or the like.

Support materials used for the silver halide color photographic light-sensitive materials of the invention include paper, glass, cellulose acetate, cellulose nitrate, polyester, polyamide, polystyrene, or laminated basic materials of more than two kinds such as paper and a polyolefin (e.g., polyethylene, polypropylene and the like). They are selectively used for each purpose. Onto the support, various surface modifying treatment are generally applied so as to improve the adhesion to silver halide emulsions. The examples thereof are a suface coarsing treatment by a mechanical method or organic solvents, a surface treatment by electron bombardment or flame and a subbing treatment by applying a subbing layer to the support.

For coating each constituent layer of silver halide color photographic light-sensitive materials onto the support, generally known methods are used, for example, a dip coating, roller coating, bead coating, curtain flow coating or the like. After coating, it is dried.

In order to obtain a color dye image on a silver halide color photographic light-sensitive material relating to the invention, a color developing process should be made after an image-wise exposure is made to light. Such processing steps fundamentally include a color developing step, a bleaching step and a fixing step. In a series of these steps, there is a case that each of the steps is processed independently, or is another case that two or more of the steps may be carried out in combination in one process with the use of a processing solution capable of functioning in the steps. A monobath type bleach-fixing liquid or the like is one of the examples of the letter. Each step may also be divided into two or more substeps, if required, to complete the process, or a color developing step, a primary fixing step, a bleach-fixing step and the like may be processed in combination with each other. Besides the abovementioned steps, a pre-hardening bath, a neutralizing bath, a primary developing (a black-and-white developing) bath, an image stabilizing bath, a washing and the like may be processed in combination, if required. A processing temperature is determined within a preferred range in accordance with the characteristics of a light-sensitive material and of a processing formula to be used. Such processing temperature is generally determined at 20° C. to 60° C., and the silver halide color photographic light-sensitive materials relating to the invention are suitably processed in particular at not lower than 30° C.

The color developing agents to be used in color developers include those which are well-known popularly used in a variety of color photographic processes.

The particularly useful color developing agents are the compounds of N,N-dialkyl-p-phenylenediamine in which the alkyl and phenyl radicals may be either substituted or not substituted. Inter alia, more particularly useful compounds include N,N-diethyl-p-phenylenediamine hydrochloride, N-methyl-p-phenylene diamine hydrochloride, N,N-dimethyl-p-phenylenediamine hydrochloride, 2-amino-5-(n-ethyl-N-dodecylamino)-toluene, N-ethyl-N-$\beta$-methanesulfonamideethyl-3-methyl-4-aminoaniline sulfate, N-ethyl-N-$\beta$-hydroxylethylaminoaniline sulfate, 4-amino-3-methyl-N,N-diethylaniline hydrochloride, N-ethyl-N-$\beta$-hydroxylethyl-3-methyl-4-aminoaniline sulfate, 4-amino-N-($\beta$-methoxyethyl)-N-ethyl-3-methylaniline-p-toluene sulfonate, and the like.

With the silver halide color photographic light-sensitive materials of the invention, excellent color dye image may be obtained even when they are processed with a color developer not containing any benzyl alcohol. It is, therefore, not necessary to add benzyl alcohol to a color developer in most cases, but it does not mean that such benzyl alcohol must not always be removed. According to circumstances, there may be some instances where they are processed with a developer added with benzyl alcohol in a small amount, say, in the amount of not more than 6 m thereof liter of a color developer.

If occasion demands, a variety of additives may be added to such color developers. The additives include, for example, an alkaline agent such as the hydroxides or carbonates of alkaline metal, or a tertiary phosphate; a buffer such as boric acid, acetic acid and the like; a development accelerator such as thioether, 1-aryl-3-pyrazolidone, N-methyl-p-aminophenol, polyalkylene glycol and the like; an organic solvent such as methanol, acetone and the like; a development inhibitor such as potassium bromide, a nitrobenzimidazole and the like; a preservative such as a sulfite, hydroxylamine, glucose, alkanolamine and the like; and a water softener such as a polyphosphoric compound, nitrilotriacetic acid and the like.

DESCRIPTION OF THE EMBODIMENTS OF THE INVENTION

Now, in the following examples are described in more details several preferred embodiments to illustrate the invention. However, it is to be understood that the invention is not intended to be limited to the specific emboiments.

EXAMPLE 1

Silver halide color photographic light-sensitive materials of six kinds (hereinafter called the Comparative Sample Nos. 1A through 6A) were prepared in the manner that each of the following layers was coated one after another onto a poly ethylene-laminated paper support.

In every one of the examples to be described hereinafter, every quantity added is indicated in terms of gram per sq. meter, unless otherwise expressly specified.

Layer 1 . . . This was a layer containing,
(a) 2.1 g of gelatin,
(b) 0.32 g (in terms of silver) of a blue-sensitive silver chlorobromide emulsion (of which silver bromide was at 85 mol % and the average grain size was 0.65 μm), and
(c) 0.3 g of dioctyl phthalate (hereinafter simply called DOP) in which $1.2 \times 10^3$ mol of yellow couplers and 0.015 g of 2,5-di-t-octyl hydroquinone (hereinafter simply called HQ-1) were dissolved.

Layer 2 . . . This was gelatin protective layer containing
(a) 1.3 g of gelatin, and
(b) 0.05 g of, bis(vinylsulfonylmethyl)ether.

On the other hand, the silver halide color photographic light-sensitive materials of the invention (hereinafter called Sample Nos. 1B through 6B of the invention) were prepared as same as the abovementioned comparative samples No. 1A through 6A, except that Layer 1 contained 0.4 g of Exemplified Compound A-1 having the Formula [I] of the invention. At that time, this Exemplified compound A-1 was dispersed in gelatin, together with the abovementioned yellow couplers.

Thus obtained six kinds of Comparative Samples (1A–6A) and six kinds of Samples of the invention (1B–6B) were exposed respectively to light through an optical wedge, and were then processed in the undermentioned steps.

Further, Color Developer (A) was of an ordinary type containing benzyl alcohol and ethylene glycol by which the benzyl alcohol was dissolved; and Color Developer (B) was that not containing any benzyl alcohol and ethylene glycol either.

| Processing Step | Temperature | Time |
|---|---|---|
| Color developing | 33° C. | 3 min. 30 sec. |
| Bleach-fixing | 33° C. | 1 30 |
| Washing | 30–34° C. | 3 |
| Drying | 60–80° C. | 2 |

The compositions of Color Developers (A), (B) and the bleach-fixing liquid were those listed below;

Color Developer (A)

| Pure water | 800 ml |
|---|---|
| Ethylene glycol | 15 ml |
| Benzyl alcohol | 15 ml |
| Hydroxylamine sulfate | 2 g |
| Potassium carbonate | 32 g |
| Potassium bromide | 0.65 g |
| Sodium chloride | 1.0 g |
| Potassium sulfite | 2.0 g |
| N—ethyl-N—$\beta$-methanesulfonamide ethyl-3-methyl-4-aminoaniline sulfate | 4.5 g |
| Whitex BB (in 50% aqueous solution) (Optical whitening agent, mfd. by Sumitomo Chemical Ind. Co., Ltd., Japan) | 2 ml |
| 1-hydroxyethylidene-1,1-diphosphonic acid (in 60% aqueous solution) | 2 ml |

Pure water was added therein to make 1 liter and the pH value thereof was adjusted by the use of 10% potassium hydroxide or dilute sulfuric acid solution to pH=10.1.

Color Developer (B)

This was that ethylene glycol and benzyl alcohol were removed from Color Developer (A).

| Bleach-fixing liquid | |
|---|---|
| Pure water | 550 ml |
| Color Developer (A) | 200 ml |
| Iron (III) ammonium ethylenediamine tetraacetic acid | 65 g |
| Ammonium thiosulfate | 85 g |
| Sodium hydrogensulfite | 10 g |
| Sodium metahydrogensulfite | 2 g |
| Di-ethylenediaminetetraacetate | 12 g |
| Sodium bromide | 10 g |
| Potassium chloride | 1.0 g |

Pure water was added thereto to make 1 liter, and the pH value was adjusted to pH=7.0 with the use of dilute sulfuric acid or concentrated aqueous ammonia.

Each of the reflection density of the samples was measured by monochromatic blue light and the results were obtained by the respective characteristic curves as shown in Table-1. Wherein, r is a gradation when a reflection density was between 0.5 and 1.5; and the relative sensitivity indicates a sensitivity relative to the sensitivity of Comparative Samples not containing exemplified compound A-1 of the invention, (1A to 6A), whose sensitivity is regarded as the value of 100 when they were processed with Color Developer (A) containing benzyl alcohol.

TABLE 1

| Sample | Yellow coupler | γ A | γ B | Relative sensitivity A | Relative sensitivity B | max. Density A | max. Density B |
|---|---|---|---|---|---|---|---|
| 1A (Out of the Invention) | Y-5 | 2.52 | 0.89 | 100 | 34 | 2.49 | 0.83 |
| 1B (Invention) | | 2.62 | 2.43 | 106 | 89 | 2.61 | 2.51 |
| 2A (Out of the Invention) | Y-6 | 2.36 | 0.98 | 100 | 40 | 2.45 | 0.99 |
| 2B (Invention) | | 2.49 | 2.19 | 110 | 85 | 2.53 | 2.46 |
| 3A (Out of the Invention) | Y-9 | 2.59 | 1.62 | 100 | 66 | 2.53 | 1.49 |
| 3B (Invention) | | 2.76 | 2.48 | 109 | 102 | 2.61 | 2.57 |
| 4A (Out of the Invention) | Y-12 | 2.40 | 0.80 | 100 | 33 | 2.49 | 1.03 |
| 4B (Invention) | | 2.61 | 2.19 | 103 | 94 | 2.51 | 2.50 |
| 5A (Out of the Invention) | Y-13 | 2.36 | 1.15 | 100 | 43 | 2.37 | 1.16 |
| 5B (Invention) | | 2.50 | 2.26 | 111 | 96 | 2.41 | 2.31 |
| 6A (Out of the Invention) | Y-15 | 2.62 | 1.84 | 100 | 76 | 2.61 | 2.03 |
| 6B (Invention) | | 2.70 | 2.60 | 108 | 104 | 2.62 | 2.59 |

It is found from the results shown in Table-1 that Samples 1B through 6B can display the excellent photographic characteristics even when they are processed with Color Developer (B) not containing benzyl alcohol at all.

EXAMPLE 2

Similar to the case of Example 1, a silver halide color photographic light-sensitive material (Sample 7) was prepared in the manner that the undermentioned two kinds of layers were coated over a paper-made support laminated thereon with polyethylene.

Layer 1 ... This was a layer containing,
(a) 2.1 g of gelatin, (b) 0.28 g of red-sensitive silver chlorobromide emulsion whose silver bromide was at 65 mol % and the average grain size was 0.35 μm, and
(c) 0.2 g of DOP in which 0.42 g of cyan coupler C-15 and 0.005 g of HQ-1 were dissolved.

Layer 2 ... This was a gelatin protective layer containing,
(a) 1.3 g of gelatin, and
(b) 0.05 g of bis(vinylsulfonylmethyl)ether.

On the other hand, Samples 8 through 11 of the invention containing 0.28 g of the exemplified compound of the invention having Formula [I] in Layer 1 were prepared respectively as shown in Talbe-2.

Thus obtained 5 kinds of Samples 7 through 11 were processed in the same manner as taken in Example 1, and the results were obtained as shown in Table-2.

TABLE 2

| | Sample | Exemplified Compound | γ Color Developer A | γ Color Developer B | Relative Sensitivity Color Developer A | Relative Sensitivity Color Developer B | Max. Density Color Developer A | Max. Density Color Developer B |
|---|---|---|---|---|---|---|---|---|
| Out of The Invention | 7 | — | 3.14 | 2.50 | 100 | 48 | 2.46 | 1.86 |
| Invention | 8 | A-1 | 3.24 | 3.09 | 101 | 86 | 2.49 | 2.37 |
| | 9 | A-5 | 3.26 | 3.13 | 99 | 84 | 2.51 | 2.43 |
| | 10 | A-9 | 3.06 | 3.11 | 104 | 90 | 2.49 | 2.46 |
| | 11 | A-10 | 3.20 | 3.16 | 106 | 92 | 2.53 | 2.45 |

In Table-2, the relative sensitivity indicates a sensitivity relative to that of comparative Sample 7 which is regarded as the value of 100 when it was processed with Color Developer (A).

It was found from the results shown in Table-2 that the silver halide color photographic light-sensitive materials 8 through 11 used therein the compounds of the invention were superior in the gradation, sensitivity and color density to Comparative Sample 7, even when they were processed with Color Developer (B).

EXAMPLE 3

A multilayered color printing paper was prepared in the manner that the undermentioned six kinds of layers were coated in order over a paper-made support laminated on the both surfaces thereof with polyethylene.

Comparative Sample (2)
Layer 1 ... This was a layer containing,
(a) 1.5 g of gelatin,
(b) 0.32 g of a blue-sensitive silver chlorobromide emulsion, and
(c) 0.3 g of DOP in which $1.2 \times 10^{-3}$ mol of yellow couplers Y-15 and 0.015 g of HQ-1 were dissolved.

Layer 2 ... This was a layer containing,
(a) 0.9 g of gelatin, and
(b) 0.06 g of DOP in which 0.09 of HQ-1 were dissolved.

Layer 3 ... This was a layer containing,
(a) 1.3 g of gelatin,
(b) 0.27 g of a green-sensitive silver chlorobromide emulsion, and
(c) 0.2 g of DOP in which $0.59 \times 10^{-3}$ mol of magenta couplers M-4 and 0.015 g of HQ-1 were dissolved.

Layer 4 ... This was a layer containing,
(a) 1.5 g of gelatin, and (b) 0.6 g of DOP in which 0.8 g of the undermentioned ultra-violet absorbent UV-1 and 0.04 g of HQ-1 were dissolved, Layer 5 . . . This was a layer containing,
(a) 1.6 g of gelatin,
(b) 0.3 g of a red-sensitive silver chlorobromide emulsion, and
(c) 0.2 g of DOP in which $0.75 \times 10^{-3}$ mol of cyan couplers C-3 and 0.005 g of HQ-1 were dissolved, and Layer 6 . . . This was a layer containing 1.0 g of gelatin.

On the other hand, a color printing paper of the invention (hereinafter called Sample 13 of the invention) was prepared, wherein Exemplified Compound A-5 of the invention was added in the amount of every 50% by weight against each of the couplers into each of the coupler dispersion liquid of the abovementioned Layer 1, 3 and of the comparative sample.

Samples 12 and 13 each thus obtained were exposed wedge-stepwise to white light, and were then processed, in the same manner as in Example 1, with color developer (A) containing benzyl alcohol and with color developer (B) not containing any benzyl alcohol, respectively. The results obtained are shown in Table-3. Wherein, B, G and R each indicate that each density was measured through each of monochromic lights in blue, green and red, respectively. The relative sensitivity indicates every value of sensitivity of B, G and R of Sample 13 of the invention relative to those of Sample 12 each regarded as the value of 100 when Sample 12 was processed with Color Developer (A).

It is found from the results shown in Table-3 that, even when processing it with Color Developer (B) not containing benzyl alcohol at all, the color printing paper relating to the invention, i.e., Sample 13 of the invention, is capable of displaying the photographic characteristics such as sensitivity, gradation and color density which are equivalent to those obtained when processing with Color Developer (A) containing benzyl alcohol in a sufficient amount, and in particular, that it is capable of maintaining the balance of the three layers in the preferable conditions.

TABLE 3

| Sample | | A | B | Relative Sensitivity A | Relative Sensitivity B | Max. Density A | Max. Density B |
|---|---|---|---|---|---|---|---|
| 12 | B | 3.14 | 1.96 | 100 | 69 | 2.53 | 1.94 |
| (Out of the | G | 3.50 | 2.41 | 100 | 81 | 2.60 | 2.50 |
| Invention) | R | 3.76 | 2.29 | 100 | 54 | 2.65 | 2.03 |
| 13 | B | 3.24 | 3.14 | 106 | 94 | 2.55 | 2.49 |
| (Invention) | G | 3.60 | 3.55 | 109 | 96 | 2.61 | 2.58 |
| | R | 3.91 | 3.80 | 103 | 92 | 2.63 | 2.51 |

What is claimed is:

1. A silver halide color photographic light-sensitive material comprising a support having thereon photographic layers containing at least one silver halide emulsion layer, wherein at least one of said photographic layers containing at least one of the compounds having the Formula [I] below;

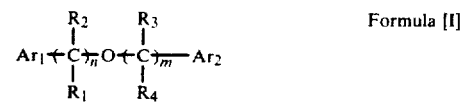

Formula [I]

wherein, $R_1$, $R_2$, $R_3$ and $R_4$ each represent hydrogen atom, or an alkyl or aryl group, $Ar_1$ and $Ar_2$ each represent an aryl group; and, n and m each have an integer of 1 or 2.

2. A silver halide color photographic light-sensitive material as claimed in claim 1, wherein the alkyl groups represented by $R_1$, $R_2$, $R_3$ and $R_4$ in the Formula [I] are those having one to six carbon atoms.

3. A silver halide color photographic light-sensitive material as claimed in claim 1, wherein the aryl groups represented by $Ar_1$ and $Ar_2$ in the Formula [I] are phenyl groups.

4. A silver halide color photographic light-sensitive material as claimed in claim 1, wherein $R_1$, $R_2$, $R_3$ and $R_4$ each represent hydrogen atom or an an alkyl group.

5. A silver halide color photographic light-sensitive material as claimed in claim 1, wherein the groups represented by $R_1$, $R_2$, $R_3$ and $R_4$ in the Formula [I] are one selected from a group of hydrogen atom, methyl group and butyl group.

6. A silver halide color photographic light-sensitive material as claimed in claim 4, wherein the groups represented by $R_1$, $R_2$, $R_3$ and $R_4$ in the Formula [I] are hydrogen atom.

7. A silver halide color photographic light-sensitive material as claimed in claim 1, wherein the compounds having the Formula [I] are contained in the silver halide emulsion layer of the photographic constituent layers.

8. A silver halide color photographic light-sensitive material as claimed in claim 1, wherein the compounds having the Formula [I] are contained in the silver halide emulsion layer containing couplers, in the proportion of 10 to 150 mol % to the couplers.

9. A silver halide color photographic light-sensitive material as claimed in claim 1, wherein the compounds having the Formula [I] are contained in the photographic constituent layers not containing any coupler, in the proportion of 0.05 to 0.5 g per sq. meter of the photographic constituent layers.

* * * * *